(12) United States Patent
Benenson et al.

(10) Patent No.: US 10,160,978 B2
(45) Date of Patent: Dec. 25, 2018

(54) PROKARYOTIC 2-COMPONENT SIGNALING PATHWAYS FOR USE AS LOGIC GATES IN MAMMALIAN CELLS

(71) Applicant: ETH Zurich, Zurich (CH)

(72) Inventors: Yaakov Benenson, Basel (CH); Jonathan Hansen, Zurich (CH); Krishna Kumar Swaminathan, Chennai (IN)

(73) Assignee: ETH ZURICH, Zurich (CH)

( * ) Notice: Subject to any disclaimer, the term of this patent is extended or adjusted under 35 U.S.C. 154(b) by 0 days.

(21) Appl. No.: 15/316,169

(22) PCT Filed: Jun. 4, 2015

(86) PCT No.: PCT/EP2015/062508
§ 371 (c)(1),
(2) Date: Dec. 4, 2016

(87) PCT Pub. No.: WO2015/185692
PCT Pub. Date: Dec. 10, 2015

(65) Prior Publication Data
US 2017/0226530 A1    Aug. 10, 2017

(30) Foreign Application Priority Data

Jun. 5, 2014 (EP) ..................... 14171271

(51) Int. Cl.
| | |
|---|---|
| *C12N 15/85* | (2006.01) |
| *C12N 15/63* | (2006.01) |
| *C12N 9/12* | (2006.01) |
| *C07K 14/435* | (2006.01) |
| *C07K 14/245* | (2006.01) |

(52) U.S. Cl.
CPC ............ *C12N 15/85* (2013.01); *C07K 14/245* (2013.01); *C07K 14/43595* (2013.01); *C12N 9/12* (2013.01); *C12N 15/635* (2013.01); *C12Y 207/13003* (2013.01); *C12N 2830/55* (2013.01)

(58) Field of Classification Search
None
See application file for complete search history.

(56) References Cited

U.S. PATENT DOCUMENTS 6,824,994 B2 * 11/2004 Weisblum .............. A61K 38/10
435/7.2

OTHER PUBLICATIONS

Antunes et al in "Programmable Ligand Detection System in Plants through a Synthetic Signal Transduction Pathway", (PLOS One, vol. 6, No. 1, Jan. 25, 2011, p. e16292) (Year: 2011).*
Close et al in "Autonomous Bioluminescent Expression of the Bacterial *Luciferase* Gene Cassette (lux) I a Mammalian Cell Line", PLOS One, vol. 5, No. 8, Aug. 27, 2010, p. e12441) (Year: 2010).*
Zhang et al in "Efficient construction of sequence-specific TAL effectors for modulating mammalian transcription", Nature Biotechnology, vol. 29, No. 2, Feb. 1, 2011, pp. 149-153) (Year: 2011).*
Rickman et al in "A two-component signal transduction system with a PAS domain-containing sensor is required for virulence of *Mycobacterium tuberculosis* in mice", (Biochemical and Biophysical Research Communications, vol. 314, No. 1, Jan. 1, 2004, pges 259-267) (Year: 2004).*
Hansen et al., "Transplantation of prokaryotic two-component signaling pathways into mammalian cells," PNAS, 111:15705-15710, 2014.
Antunes et al., "Programmable Ligand Detection System in Plants trough a Synthetic Signal Transduction Pathway," PLOS One, 6:e16292, 2011 (11 pages).
Close et al., "Autonomous Bioluminescent Expression of the Bacterial *Luciferase* Gene Cassette (lux) in a Mammalian Cell Line," PLOS One, 5:e12441, 2010 (12 pages).
Zhang et al., "Efficient construction of sequence-specific TAL effectors for modulating mammalian transcription," Nature Biotech., 29:149-153, 2011.
Besant et al., "Mammalian histidine kinases," Biochim Biophys Acta, 1754:281-290, 2005.
Chen et al., "Transplantation of prokaryotic two-component signaling pathways into mammalian cells," Genome Biology, 13:240, 2012 (10 pages).
Rickman et al., "A two-component signal transduction system with a PAS domain-containing sensor is required for virulence of *Mycobacterium tuberculosis* in mice," Biochem Biophys Res Comm, 314:259-267, 2004.

* cited by examiner

*Primary Examiner* — Catherine S Hibbert
(74) *Attorney, Agent, or Firm* — JMB Davis Ben-David

(57) ABSTRACT

The invention relates to mammalian cells comprising at least one prokaryotic two-component signaling (TCS) pathway comprised of an activator protein A, a response regulator (RR) protein B activated by said protein A, such activation leading to an activated RR protein B, and an output gene C operably linked to a promoter. Transcription from said promoter is activated by activated RR protein B, and the expression of output gene C defines at least a first state (0, no transcription) and a second state (1, detectable transcription). The invention further relates to logic gates designed from such cells, and methods for integrating a plurality of output signals based on the cells and logic gates of the invention.

Figure 1:
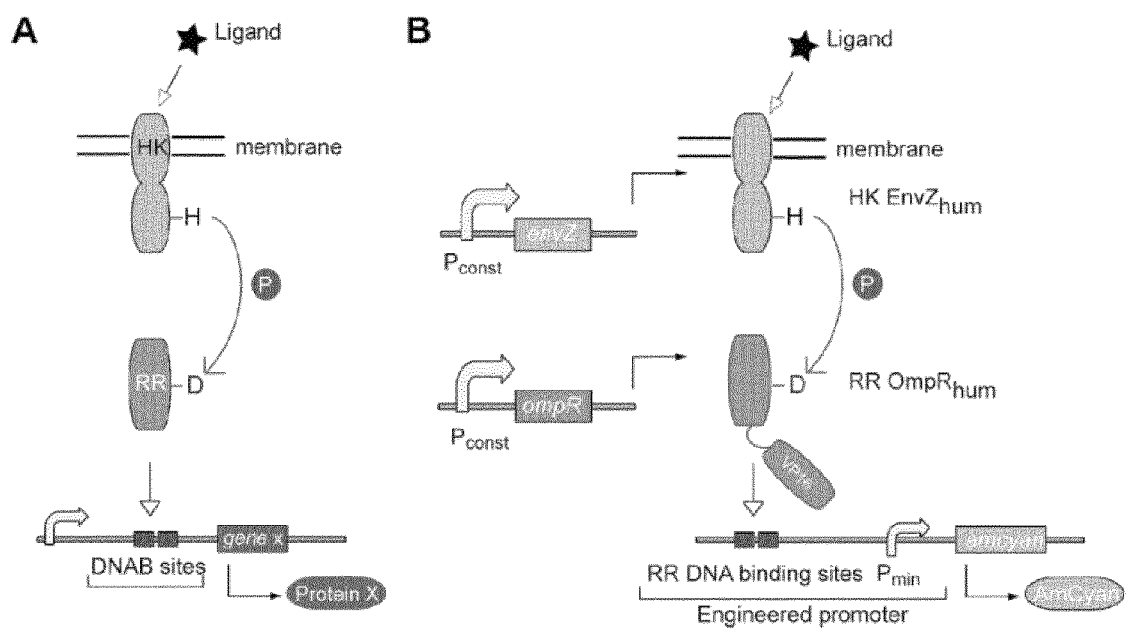

14 Claims, 8 Drawing Sheets
Specification includes a Sequence Listing.

Fig. 5

KEGG

| Entry | PATHWAY: map02020 |
|---|---|
| Name | Two-component system |
| Description | Two-component signal transduction systems enable bacteria to sense, respond, and adapt to changes in their environment or in their intracellular state. Each two-component system consists of a sensor protein-histidine kinase (HK) and a response regulator (RR). In the prototypical two-component pathway, the sensor HK phosphorylates its own conserved His residue in response to a signal(s) in the environment. Subsequently, the phosphoryl group of HK is transferred onto a specific Asp residue on the RR. The activated RR can then effect changes in cellular physiology, often by regulating gene expression. Two-component pathways thus often enable cells to sense and respond to stimuli by inducing changes in transcription. |
| Class | Environmental Information Processing; Signal transduction<br>BRITE hierarchy |
| Module | |
| M00314 | Bacitracin transport system [PATH:map02020] |
| M00315 | Uncharacterized ABC transport system [PATH:map02020] |
| M00316 | Manganese transport system [PATH:map02020] |
| M00434 | PhoR-PhoB (phosphate starvation response) two-component regulatory system [PATH:map02020] |
| M00443 | SenX3-RegX3 (phosphate starvation response) two-component regulatory system [PATH:map02020] |
| M00444 | PhoQ-PhoP (magnesium transport) two-component regulatory system [PATH:map02020] |
| M00445 | EnvZ-OmpR (osmotic stress response) two-component regulatory system [PATH:map02020] |
| M00446 | RstB-RstA two-component regulatory system [PATH:map02020] |
| M00447 | CpxA-CpxR (envelope stress response) two-component regulatory system [PATH:map02020] |
| M00448 | CssS-CssR (secretion stress response) two-component regulatory system [PATH:map02020] |
| M00449 | CreC-CreB (phosphate regulation) two-component regulatory system [PATH:map02020] |
| M00450 | BaeS-BaeR (envelope stress response) two-component regulatory system [PATH:map02020] |
| M00451 | BasS-BasR (antimicrobial peptide resistance) two-component regulatory system [PATH:map02020] |
| M00452 | CusS-CusR (copper tolerance) two-component regulatory system [PATH:map02020] |
| M00453 | QseC-QseB (quorum sensing) two-component regulatory system [PATH:map02020] |
| M00454 | KdpD-KdpE (potassium transport) two-component regulatory system [PATH:map02020] |
| M00455 | TorS-TorR (TMAO respiration) two-component regulatory system [PATH:map02020] |
| M00456 | ArcB-ArcA (anoxic redox control) two-component regulatory system [PATH:map02020] |
| M00457 | TctE-TctD (tricarboxylic acid transport) two-component regulatory system [PATH:map02020] |
| M00458 | ResE-ResD (aerobic and anaerobic respiration) two-component regulatory system [PATH:map02020] |

Fig. 5 continued

| M00459 | VicK-VicR (cell wall metabolism) two-component regulatory system [PATH:map02020] |
| --- | --- |
| M00460 | MprB-MprA (maintenance of persistent infection) two-component regulatory system [PATH:map02020] |
| M00461 | MtrB-MtrA (osmotic stress response) two-component regulatory system [PATH:map02020] |
| M00462 | PrrB-PrrA (intracellular multiplication) two-component regulatory system [PATH:map02020] |
| M00463 | TrcS-TrcR two-component regulatory system [PATH:map02020] |
| M00464 | NrsS-NrsR (nickel tolerance) two-component regulatory system [PATH:map02020] |
| M00465 | ManS-ManR (manganese homeostasis) two-component regulatory system [PATH:map02020] |
| M00466 | NblS-NblR (photosynthesis) two-component regulatory system [PATH:map02020] |
| M00467 | SasA-RpaAB (circadian timing mediating) two-component regulatory system [PATH:map02020] |
| M00468 | SaeS-SaeR (staphylococcal virulence regulation) two-component regulatory system [PATH:map02020] |
| M00469 | BceS-BceR (bacitracin transport) two-component regulatory system [PATH:map02020] |
| M00470 | YxdK-YxdJ (antimicrobial peptide response) two-component regulatory system [PATH:map02020] |
| M00471 | NarX-NarL (nitrate respiration) two-component regulatory system [PATH:map02020] |
| M00472 | NarQ-NarP (nitrate respiration) two-component regulatory system [PATH:map02020] |
| M00473 | UhpB-UhpA (hexose phosphates uptake) two-component regulatory system [PATH:map02020] |
| M00474 | RcsC-RcsD-RcsB (capsule synthesis) two-component regulatory system [PATH:map02020] |
| M00475 | BarA-UvrY (central carbon metabolism) two-component regulatory system [PATH:map02020] |
| M00476 | ComP-ComA (competence) two-component regulatory system [PATH:map02020] |
| M00477 | EvgS-EvgA (acid and drug tolerance) two-component regulatory system [PATH:map02020] |
| M00478 | DegS-DegU (multicellular behavior control) two-component regulatory system [PATH:map02020] |
| M00479 | DesK-DesR (membrane lipid fluidity regulation) two-component regulatory system [PATH:map02020] |
| M00480 | VraS-VraR (cell-wall peptidoglycan synthesis) two-component regulatory system [PATH:map02020] |
| M00481 | LiaS-LiaR (cell wall stress response) two-component regulatory system [PATH:map02020] |
| M00482 | DevS-DevR (redox response) two-component regulatory system [PATH:map02020] |
| M00483 | NreB-NreC (dissimilatory nitrate/nitrite reduction) two-component regulatory system [PATH:map02020] |
| M00484 | YdfH-YdfI two-component regulatory system [PATH:map02020] |
| M00485 | KinABCDE-Spo0FA (sporulation control) two-component regulatory system [PATH:map02020] |
| M00486 | CitA-CitB (citrate fermentation) two-component regulatory system [PATH:map02020] |
| M00487 | CitS-CitT (magnesium-citrate transport) two-component regulatory system [PATH:map02020] |

Fig. 5 continued

| M00488 | DcuS-DcuR (C4-dicarboxylate metabolism) two-component regulatory system [PATH:map02020] |
| M00489 | DctS-DctR (C4-dicarboxylate transport) two-component regulatory system [PATH:map02020] |
| M00490 | MalK-MalR (malate transport) two-component regulatory system [PATH:map02020] |
| M00492 | LytS-LytR two-component regulatory system [PATH:map02020] |
| M00493 | AlgZ-AlgR (alginate production) two-component regulatory system [PATH:map02020] |
| M00494 | NatK-NatR (sodium extrusion) two-component regulatory system [PATH:map02020] |
| M00495 | AgrC-AgrA (exoprotein synthesis) two-component regulatory system [PATH:map02020] |
| M00496 | ComD-ComE (competence) two-component regulatory system [PATH:map02020] |
| M00497 | GlnL-GlnG (nitrogen regulation) two-component regulatory system [PATH:map02020] |
| M00498 | NtrY-NtrX (nitrogen regulation) two-component regulatory system [PATH:map02020] |
| M00499 | HydH-HydG (metal tolerance) two-component regulatory system [PATH:map02020] |
| M00500 | AtoS-AtoC (cPHB biosynthesis) two-component regulatory system [PATH:map02020] |
| M00501 | PilS-PilR (type 4 fimbriae synthesis) two-component regulatory system [PATH:map02020] |
| M00502 | GlrK-GlrR (amino sugar metabolism) two-component regulatory system [PATH:map02020] |
| M00503 | PgtB-PgtA (phosphoglycerate transport) two-component regulatory system [PATH:map02020] |
| M00504 | DctB-DctD (C4-dicarboxylate transport) two-component regulatory system [PATH:map02020] |
| M00505 | KinB-AlgB (alginate production) two-component regulatory system [PATH:map02020] |
| M00506 | CheA-CheYBV (chemotaxis) two-component regulatory system [PATH:map02020] |
| M00507 | ChpA-ChpB/PilGH (chemosensory) two-component regulatory system [PATH:map02020] |
| M00508 | PixL-PixGH (positive phototaxis) two-component regulatory system [PATH:map02020] |
| M00509 | WspE-WspRF (chemosensory) two-component regulatory system [PATH:map02020] |
| M00510 | Cph1-Rep1 (light response) two-component regulatory system [PATH:map02020] |
| M00511 | PleC-PleD (cell fate control) two-component regulatory system [PATH:map02020] |
| M00512 | CckA-CtrA/CpdR (cell cycle control) two-component regulatory system [PATH:map02020] |
| M00513 | LuxQN/CqsS-LuxU-LuxO (quorum sensing) two-component regulatory system [PATH:map02020] |
| M00514 | TtrS-TtrR (tetrathionate respiration) two-component regulatory system [PATH:map02020] |
| M00515 | FlrB-FlrC (polar flagellar synthesis) two-component regulatory system [PATH:map02020] |
| M00516 | SLN1-YPD1-SSK1/SKN7 (osmosensing) two-component regulatory system [PATH:map02020] |
| M00517 | RpfC-RpfG (cell-to-cell signaling) two-component regulatory system |

Fig. 5 continued

| | [PATH:map02020] |
|---|---|
| M00518 | GlnK-GlnL (glutamine utilization) two-component regulatory system [PATH:map02020] |
| M00519 | YesM-YesN two-component regulatory system [PATH:map02020] |
| M00520 | ChvG-ChvI (acidity sensing) two-component regulatory system [PATH:map02020] |
| M00521 | CiaH-CiaR two-component regulatory system [PATH:map02020] |
| M00522 | SalK-SalR two-component regulatory system [PATH:map02020] |
| M00523 | RegB-RegA (redox response) two-component regulatory system [PATH:map02020] |
| M00524 | FixL-FixJ (nitrogen fixation) two-component regulatory system [PATH:map02020] |

Obtained from: http://www.genome.jp/dbget-bin/www_bget?pathway:map02020

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: consensus sequence of the OmpR response element

<400> SEQUENCE: 1
atttacattt tgaaacatct a                                              21

<210> SEQ ID NO 2
<211> LENGTH: 16
<212> TYPE: DNA
<213> ORGANISM: Artificial Sequence
<220> FEATURE:
<223> OTHER INFORMATION: consensus sequence of the NarL response element

<400> SEQUENCE: 2 taccccctata ggggta                                                   16

<210> SEQ ID NO 3
<211> LENGTH: 24
<212> TYPE: DNA
<213> ORGANISM: Artificial Sequence
<220> FEATURE:
<223> OTHER INFORMATION: constructed DcuR response element

<400> SEQUENCE: 3
tgattaaaac tttaaaaagt gctg                                           24
```

PROKARYOTIC 2-COMPONENT SIGNALING PATHWAYS FOR USE AS LOGIC GATES IN MAMMALIAN CELLS

CROSS-REFERENCE TO RELATED APPLICATIONS

This is the U.S. National Stage of International Application No. PCT/EP2015/062508, filed Jun. 4, 2015, which was published in English under PCT Article 21(2), and which in turn claims the benefit of European Patent Application No. 14171271.1 filed on Jun. 5, 2014.

Signaling pathways are the cell's major interface with the environment and many strategies have evolved for signaling in the different kingdoms of life. Functionally all signaling pathways share common features, such as i) a membrane receptor that responds to an external ligand; ii) a number of downstream components used to amplify weak signals, filter noise, sharpen the response, perform adaptation, etc., and iii) at the receiving end, appropriate genetic and protein motifs.

Virtually all these pathways use catalytic, posttranslational phosphoryl transfer to transmit information, resulting in much faster response timescales compared to transcriptional or post-transcriptional control. Since the systems rely on protein-protein interactions, substantial modularity has evolved with tens if not hundreds of pathways encoded and expressed simultaneously in cell genomes. At the same time, this modularity is complemented with inter-pathway communication via crosstalk and a plethora or one-to-many or many-to-one input-output relationships. In the context of synthetic biology, signaling represents a challenging case. Because of their heavy use of proteins, any pathway modification requires protein re-engineering or de-novo protein design.

Therefore "transkingdom pathway transplantation", which, as the name implies, involves transplantation of a pathway from an evolutionarily distinct donor into the host cell can be used to overcome this problem. Re-design of a native pathway often carries a risk of unwanted interactions with the other pathways. However, introduction of a completely foreign pathway ideally from the donor that is as divergent as possible from the recipient, can minimize this risk. The application of phage-derived recombinases and prokaryotic-based transcription regulators are known in the art.

Two-component signaling (TCS) pathways are ubiquitous in prokaryotes, comprising in their simplest form a sensor and regulator components. The sensor histidine kinase (HK) typically has extracellular and cytoplasmic domains linked via a transmembrane domain. Upon ligand binding, typically to the extracellular domain and subsequent conformational change, autophosphorylation of the conserved histidine residue in the cytoplasmic domain takes place. The phosphate is then transferred to the aspartic residue on the response regulator (RR), inducing a conformation change that usually facilitates DNA binding. Thus, phosphorylated, homodimerized RR can bind to an appropriate DNA motif and modulate gene expression. In other cases such as chemotaxis, two-component signaling results in posttranslational modifications of downstream proteins. The biochemical process of phosphoryl transfer from a histidine to aspartate residue is encountered in plants and low eukaryotes while it is all but absent in vertebrates, where tyrosine-serine/threonine phosphorelay is the rule.

The present invention relates to the implementation of prokaryotic signaling in mammalian cells. Known in the art is re-wiring and synthetic application in prokaryotic cells (Levskaya et al., Nature, 2005, 438(7067), 441-442; Skerker et al., Cell 2008, 133(6), 1043-1054; Tabor et al., Cell 2009, 137(7), 1272-1281) as well as *Arabidopsis* (Ninfa et al., COiM 2010, 13(2), 240-245; Antunes et al., Plos ONE 6(1)). Whereas Urao et al. (Plant Cell, 1999. 11(9), 1743-1754) teaches the functional complementation by a plant-derived HK in yeast. However, the adaptation of a TCS system to mammalian cells is not known in the art. This invention discloses such adaptation and teaches that the internal core of the pathways and their specific interactions continue to be functional in mammalian cells. At the same time, the sensing of extracellular inputs has not been observed. The transplanted modules can be utilized to implement complex logical programs of gene expression. In addition, the pathway genes may serve as a rich source of orthogonal building blocks for engineering genetic circuits in mammalian cells.

The problem underlying the present invention is to provide engineered orthogonal signaling pathways for use in mammalian cells. This problem is solved by the subject-matter of the independent claims.

Terms and Definitions

In the context of the present specification, the term "orthogonal" refers to the independence of a signaling pathway or part thereof to other signaling pathways. In other words an orthogonal signaling pathway would not experience crosstalk with other endogenous signaling pathways.

In the context of the present specification, the term "biological logic gate" refers to a signaling pathway that integrates signals analogous to electronic logic gates with an output activity that is activated only upon stimulation with the appropriate combination of inputs. According to the combination of input signals required to generate an output signal different kinds of logic gates are defined (AND, OR, NOR, NAND etc.). Examples of required input signals for different kinds of logic gates are given in table 1. Just as electronic logic gates can be wired together to generate an infinite diversity of complex circuits, biological logic gates can be combined to generate their diverse control circuits.

TABLE 1

A value of 0 means inactive and 1 means active

| Type | Input 1 | Input 2 | Output | Type | Input 1 | Input 2 | Output |
|---|---|---|---|---|---|---|---|
| AND | 0 | 0 | 0 | NOR | 0 | 0 | 1 |
|  | 0 | 1 | 0 |  | 0 | 1 | 0 |
|  | 1 | 0 | 0 |  | 1 | 0 | 0 |
|  | 1 | 1 | 1 |  | 1 | 1 | 0 |
| OR | 0 | 0 | 0 | NAND | 0 | 0 | 1 |
|  | 0 | 1 | 1 |  | 0 | 1 | 1 |
|  | 1 | 0 | 1 |  | 1 | 0 | 1 |
|  | 1 | 1 | 1 |  | 1 | 1 | 0 |

According to a first aspect of the invention, a mammalian cell comprising a prokaryotic two-component signaling (TCS) pathway is provided. This TCS comprises an activator protein A, which activates a response regulator (RR) protein B and an output gene C that is operably linked to a promoter. The activated RR protein B is able to activate the promoter linked to output gene C and the expression of output gene C defines at least a first state (0, no transcription) and a second state (1, detectable transcription).

In certain embodiments the activator protein A is a histidine kinase molecule selected from envZ, NarX, DcuS and examples in FIG. 5.

In certain embodiments the RR protein B is a transcriptional regulator selected from ompR, NarL, DcuR and examples in FIG. 5.

In certain embodiments the output gene encodes a fluorescent reporter, a protein or microRNA that affects the cell function or internal state. In certain embodiments the output gene C is amcyan.

In certain embodiments the activator protein A can be constitutively active or activated by input signals. The input signals are selected from: quinones, nitrate, nitrite, citrate, isocitrate, fumarate, succinate, malate, indole, serine, aspartate, chemoattractants, oxygen, carbon monoxide, nitrous oxide, blue light, vancomycin, potassium, quorum sensing molecules, temperature change, sulfate ions, nicotinic acid, changes in osmolarity, toluene, O-xylene, glutamine, 2-ketoglutarate, magnesium.

According to a second aspect of the invention, an engineered biological logic AND gate is provided. The logic AND gate comprises the mammalian cell according to the first aspect of the invention, wherein input 1 activates the activator protein A, input 2 activates the response regulator protein and the output is the expression state of output gene C.

In certain embodiments input 2 activates a second activator protein A', which is able to activate a second RR protein B' that enables transcription of the first response regulator protein B.

In certain embodiments input 1 and input 2 can be input signals according to other embodiments or stimuli controlling expression of the components such as transcription factors or microRNAs.

According to a third aspect of the invention, an engineered biological logic OR gate is provided. The logic OR gate comprises the mammalian cell according to the first aspect of the invention, wherein input 1 activates said activator protein A, input 2 activates a second activator protein A', which is able to activate the same RR protein B as activator protein A. The output of the logic OR gate is the expression state of said output gene C.

According to a fourth aspect of the invention, an engineered biological logic NOR gate is provided. The logic gates comprises the mammalian cell according to the first aspect of the invention, wherein input 1 is an inhibitor A− of said activator protein A, input 2 is an inhibitor B− of said RR protein B and the output is the expression state of said output gene C.

According to a fifth aspect of the invention, an engineered biological logic NAND gate is provided. The logic gates comprises the mammalian cell according to the first aspect of the invention, wherein input 1 is an inhibitor A− of said activator protein A, input 2 is an inhibitor A'− of said activator protein A' and the output is the expression state of said output gene C.

According to a sixth aspect of the invention, a method for integrating a plurality of input signals and transducing them into an output signal is provided. This method comprises at least one of the engineered biological logic gates according to the other aspects of the invention.

In certain embodiments the input signals are selected from a biological agent, a chemical agent, a metal ion, a toxin, and a pollutant.

In certain embodiments the output signal changes its state if the plurality of signals is specific for an environmental condition, a pollutant, a pharmaceutical substance or prodrug, or a disease state.

In certain embodiments the two component system inside the mammalian cell according to the aspects of the invention is a reporter system for changes in the internal/external state of the cell. In other words constitutively expressed TCS proteins can monitor internal chemical signals from endogenous signaling pathways and/or external chemical signals.

In certain embodiments the two component system inside the mammalian cell according to the aspects of the invention is a positive feedback amplifier. In other words constitutive activation of the TCS pathway acts as a positive feedback amplifier by controlling the pathway output with the pre-motor of the output gene C, which does not cross react with mammalian cell transcription factors.

In certain embodiments the two component system inside the mammalian cell according to the aspects of the invention integrates signals from different pathways to modify the mammalian cell. In other words by integrating signals from different pathways or using the logic gates according to the aspects of the invention these signals can provide a reporter fluorescent output or the production of proteins to interact with endogenous cell pathways; thus, modifying the cell in which this pathway is active.

In certain embodiments the proteins of the two component system inside the mammalian cell according to the aspects of the invention are constitutively active and are utilized in overexpression of products within the cell by increasing expression as a feedback amplifier.

In certain embodiments the proteins of the two component system inside the mammalian cell according to the aspects of the invention are constitutively active and are utilized as material in gene circuits. In certain embodiments these circuits are controlled with endogenous sensors or with transcription factor sensors, exploiting the constitutive properties of the TCS configurations provided in the examples. In certain embodiments amplification of circuit modules can be accomplished with constitutively active mutant proteins.

In certain embodiments to all aspects of the invention the output gene C could encode a protein or microRNA that affects the cell function or internal state. This could be helpful in temporal processes such as drug deployment or drug target expression.

In certain embodiments to all aspects of the invention the output gene C could encode a fluorescent reporter protein.

In certain embodiments of the invention NOR and NAND gates can be combined to produce any gate logic.

The invention is further illustrated by the following examples and figures, from which further embodiments and advantages can be drawn. These examples are meant to illustrate the invention but not to limit its scope.

SHORT DESCRIPTION OF THE FIGURES

FIG. 1 shows the schematics of native and transplanted two-component signaling pathways. A, The native pathway architecture consists of a receptor protein, which senses and propagates a signal to a cognate response regulator that activates gene expression. B, The envisioned adaptation to the mammalian host exemplified with EnvZ-OmpR pathway.

Figure 2:
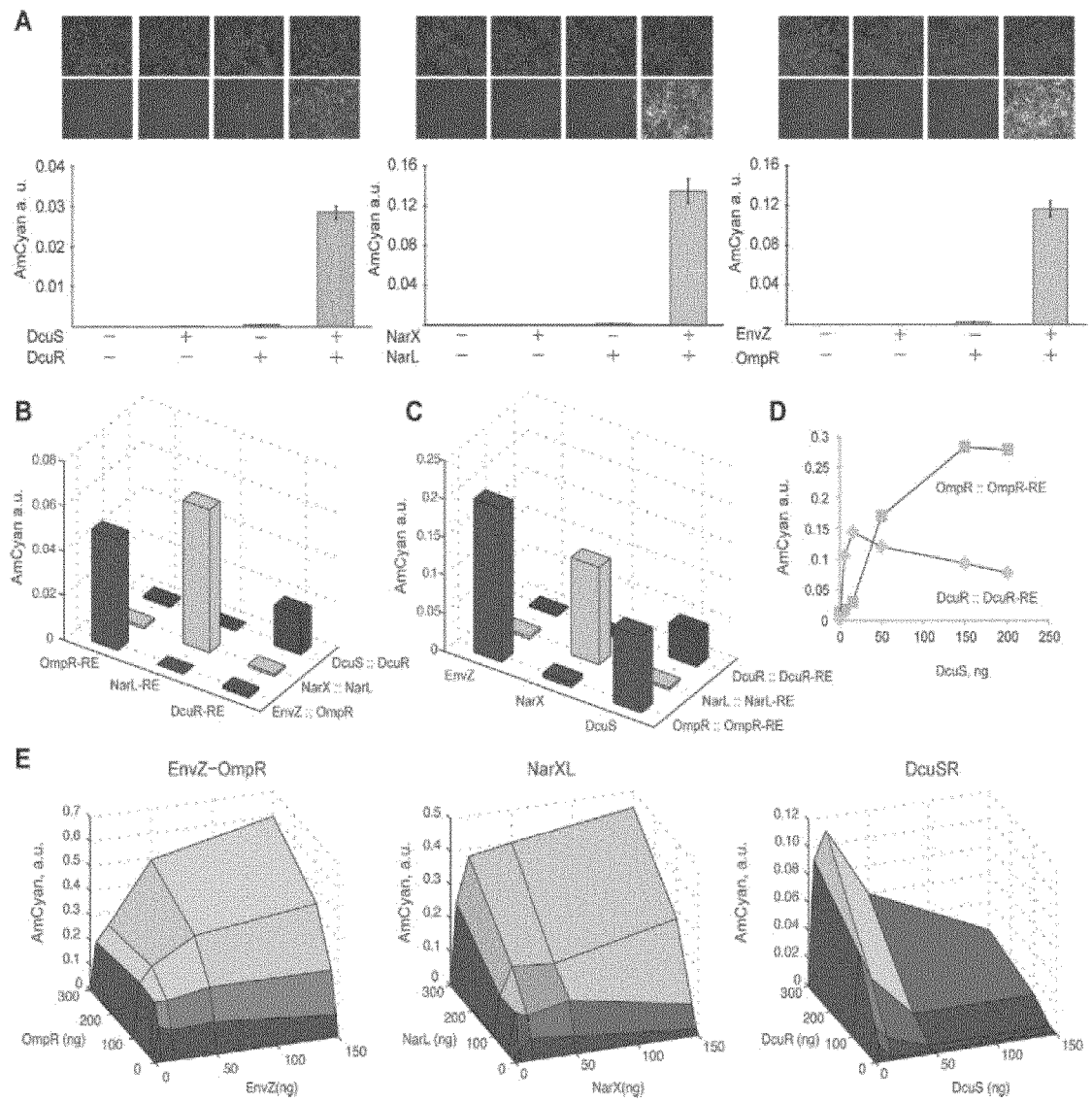

FIG. 2 shows basic characterization of the transplanted two-component pathways. A, Component requirements for response element activation. Each component combination is accompanied by representative microscopy pictures with red pseudocolor indicating the expression of DsRed transfection marker, and cyan pseudocolor indicating the expression of the AmCyan pathway output. The bar charts display AmCyan level in a.u. as mean±SD of independent biological triplicates. B, Cross-talk of HK::RR pairs with non-cognate response elements. C, Cross-talk of non-cognate HKs with RR::RE pairs, indicating that DcuS phosphorylates OmpR. D, Detailed look into the DcuS-OmpR cross-talk. DcuS-OmpR interaction is displayed using blue markers and cognate DcuS-DcuR is shown with red markers. Each data point is the average of independent duplicate measurement. E, The relationship between the amounts of HKs and RRs and the intensity of a reporter gene expression. For each surface plot, all pairwise combinations of HK and RR were measured with HK added at 0, 5, 50 and 150 ng per transfection in a 12-well plate and RR added at 0, 10, 30, 100 and 300 ng. Filler DNA was added to keep the total DNA amount constant. All data points are duplicate averages.

Figure 3:
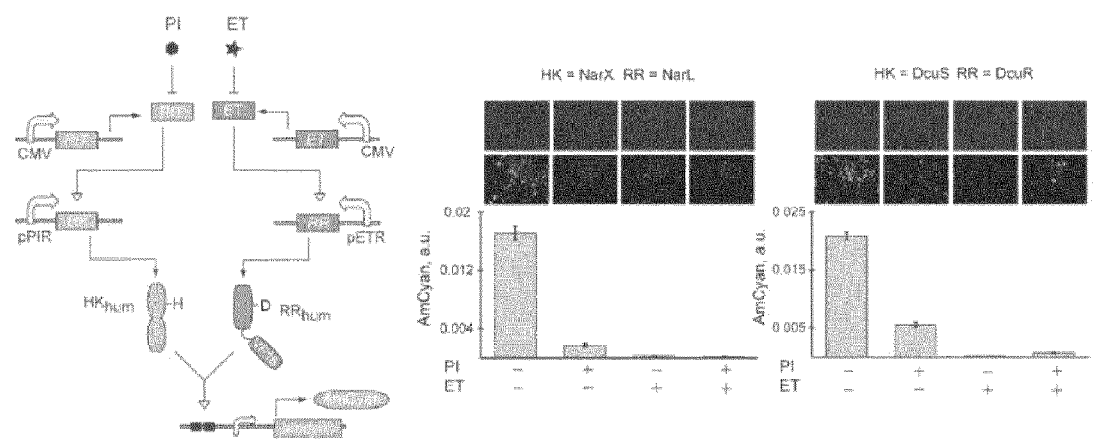

FIG. 3 shows complex control of gene expression with TCS pathways using antibiotic-controlled HK and RR genes. Circuit schematics are shown on the left and quantitative data for NarXL and DcuSR pathways are on the right. CMV-driven PIT2 and ET proteins activate HK and RR via pPIR and pETR promoters, respectively. The final concentration of PI and ET was 10 µg/ml and 4 µg/ml, respectively. The resultant data are presented as mean±SD of biological triplicates. Microscopy images are shown with red pseudocolor indicating the expression of DsRed transfection marker, and cyan pseudocolor indicating the expression of the AmCyan pathway output.

Figure 4:
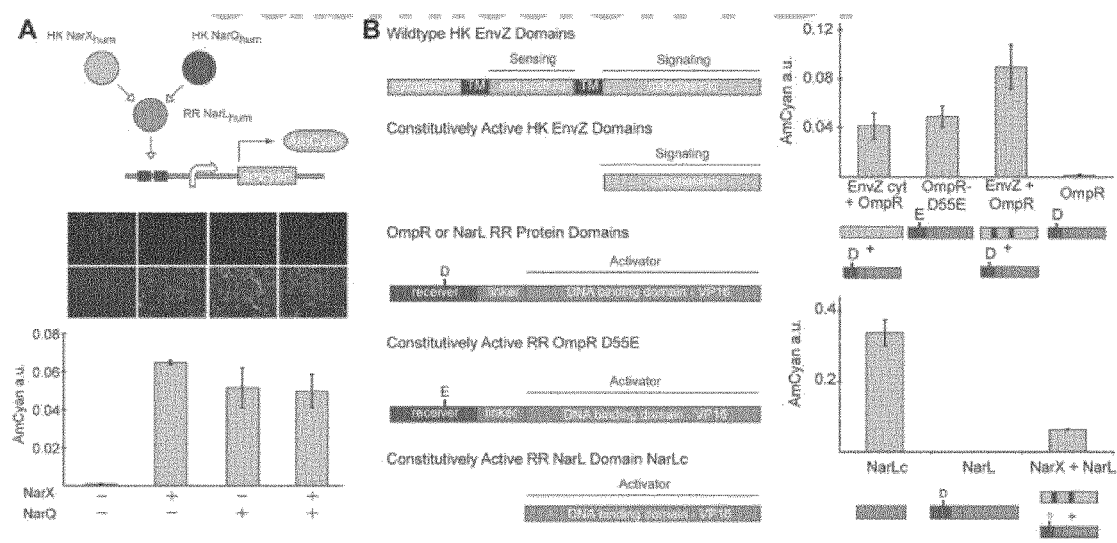

FIG. 4 shows utilization of TCS pathways and individual components for mammalian gene expression. A, Gene expression controlled by an OR gate configuration. Top, schematic representation of an OR gate using the presence of NarX and NarQ as inputs. Bottom, the quantification of the gate shown as mean±SD of biological triplicates with representative microscopy photos. The images are shown with red pseudocolor indicating the expression of DsRed transfection marker (top panel), and cyan pseudocolor indicating the expression of the AmCyan pathway output (lower panel). B, Activity of various mutant TCS components. Full-length, truncated and mutant TCS genes are represented with each protein domain color-coded and labeled. Experimental data are shown on the right. Each bar represents mean±SD of a biological triplicate. The output values for NarX+NarL and NarL were taken from the experiment in panel A; their results are again displayed in panel B merely for side-by-side comparison.

FIG. 5 shows examples of two-component signaling pathways in bacteria.

EXAMPLES

Signaling pathway engineering is a route toward synthetic biological circuits. Histidine-aspartate phosphorelays are thought to have evolved in prokaryotes where they form the basis for two-component signaling. Tyrosine-serine/threonine phosphorelays, exemplified by MAP kinase cascades, are predominant in eukaryotes. Rational re-wiring of these pathway families are known in the art. One example known in the art is the implementation of a prokaryotic two-component pathway in a plant species to sense environmental TNT. In this invention the inventors disclose the "transplantation" of two-component pathways into mammalian cells to provide an orthogonal and diverse toolkit for a variety of signal processing tasks. The inventors use two-component pathways in mammalian cell culture and use them for programmable control of gene expression. Therefore, coding sequences of histidine kinase (HK) and response regulator (RR) components were codon-optimized for human cells, while the RRs were fused with a transactivation domain. Responsive promoters were furnished by fusing DNA binding sites in front of a minimal promoter.

The inventors disclose examples that co-expression of HKs and their cognate RRs in cultured mammalian cells are sufficient to strongly induce gene expression even in the absence of pathways' chemical triggers. Mutants that were constitutive in the native setting showed similar behavior in mammalian cells. The inventors further used the TCS pathways to implement two-input logical AND, NOR and OR gene regulation using inducible promoters to drive HKs and RRs. Thus, two component systems can be applied in different capacities in mammalian cells and their components can be utilized for large-scale synthetic gene circuits.

TCS is Partially Functional in Mammalian Cells

Transplanting prokaryotic TCS pathways to mammalian cell lines requires a number of necessary adaptations (FIG. 1B). Each gene coding for a TCS protein was codon-optimized to confer to human codon usage; furthermore they were placed under constitutive CMV immediate early promoter. The basic amino acid sequence of each HK and RR was preserved, while the RR sequences were augmented with 3×minimal VP16 transactivating domain at the C-terminus. (Note that nuclear localization signal was not fused to RRs.) Finally, the responsive promoter driving a fluorescent reporter AmCyan was created by fusing DNA binding sites of different RRs in front of a mammalian minimal promoter.

Three TCS pathways from *E. Coli* were selected and adapted to mammalian cells, including EnvZ-OmpR, NarXL and DcuSR. The design of adapted HKs and RRs was performed as described above, while the design of responsive promoters varied from case to case. For the OmpR response element (OmpR-RE), a consensus sequence ATTTACATTTTGAAACATCTA (SEQ ID NO. 1) was used. Two copies of this sequence were separated by 10-bp spacer and inserted 18 bp upstream of the TATA box in the Core Minimal Promoter. For NarL response element (NarL-RE), a consensus sequence TACCCCTATAGGGGTA (SEQ ID NO. 2) was used; two copies separated by 10 bp were used identically to the OmpR-RE above. Finally, for the DcuR-sensitive promoter, DcuR response element was constructed using a single inverted repeat sequence TGATTAAAACTT-TAAA-AAGTGCTG (SEQ ID NO. 3) identified in the dctA gene promoter region. The aforementioned regulated promoters were cloned upstream from the fluorescent protein AmCyan.

First the inventors inquired whether coexpression of the pathway genes in cultured human cells would result in gene activation. They performed transient transfections into HEK293 cells with (i) none of the TCS expression cassettes; (ii) HK or RR cassettes alone and (iii) both HK and RR. All three pathways elicit strong expression of the reporter gene when both the HK and RR are present but not when either components is missing (FIG. 2A). The induction with DcuSR was weaker, perhaps due to having a single rather than a double DNA binding site in the promoter. These results indicates that major features of the pathways, such as protein folding, phosphorelay, and differential DNA binding and transactivation, are operational in human cells. At the same time, gene induction occurs in the absence of cognate external stimulus. While EnvZ-OmpR and NarXL pathways respond to generic inputs that could be present in the medium, DcuSR is responsive to fumarate. We performed fumarate titration and did not find clear evidence for pathway induction as most of the activity was already present at zero fumarate. Intermediate levels of fumarate seem to increase the output modestly, but even higher levels were inhibitory. Additionally, the RRs do not seem to be phosphorylated by the native kinases of HEK293 cells, as evidenced by low output expression level in the presence of RR alone.

TCS Orthogonality and Crosstalk in Human Cells

Multiple TCS function without extensive crosstalk in their endogenous milieu. Being able to operate multiple pathways in parallel would allow facile scaling up of genetic circuits. First, the canonical HK::RR pairs were kept together but the response elements were varied (FIG. 2B). The activation is highly-specific to the correct responsive promoter. In the second experiment, the RRs were combined with their cognate responsive promoter and the upstream HK was varied. In one case the inventors observed that an HK DcuS activates a non-cognate RR OmpR while in all other cases the phosphorelay is specific (FIG. 2C). The dose-response of the cognate as well as non-cognate DcuS activity was further investigated (FIG. 2D). The result shows markedly distinct behavior between the two cases. The correctly-assembled pathway exhibits sharp dose-response that decreases upon further increase in DcuS. At the same time, the cross-reactivity shows a monotonous and slow increase. Indeed, operating at the optimal level of humanized DcuS would result in high selectivity toward the cognate pathway.

Next the input-output relationship of the transplanted pathways was mapped. Therefore the amount of the response plasmid were fixed and the amounts of both HK and RR—encoding plasmids was varied (FIG. 2E). All pathways show marked sensitivity to the amount of HK, which is unsurprising given its enzymatic nature. The dependency on the amount of RR is gradual; however half the maximum induction is reached with very low amounts of both HK and RR relative to the response gene. The input-output map of DcuSR pathway reproduces the non-monotonous behavior observed in FIG. 2D. The possible reason for this behavior is that the dephosphorylated form of DcuS acts as a phosphatase for DcuR-P, similar to other histidine kinases.

TCSs as Building Blocks for Genetic Logic Circuits

The experiments above show that the response requires expression of both pathway components. Such mode of operation is often described as an AND logic with the inputs in this case being the expression of HK and RR, respectively. Controlling these genes with external stimuli will generate additional logic behaviors. To exemplify this possibility, the inventors cloned the components of NarXL and DcuSR pathways in vectors controlled by engineered transactivators PIT2 (Fussenegger et al., Nat Biotech 200, 18(11), 1203-1208) and ET (Weber et al., Nat Biotech, 20(9), 901-907). This allowed for antibiotics erythromycin (ET) and pristinamycin 1A (PI) to control the circuit output. Since both cofactors are inhibitors of DNA binding of their cognate transactivators, the underlying AND logic translates into NOR logic when the antibiotics comprise the external inputs (FIG. 3). The resultant logic behavior is consistent with expectation (highest output in the absence of both inputs, low output otherwise). The NarXL pathway displays the largest dynamic range, while with DcuSR pathway the leakage in one of the OFF states is likely due to very high sensitivity of this pathway to minute amounts of the DcuS HK and residual expression of DcuS in the presence of PI. The low level of induction in the ON state is due to multiple plasmid cotransfection.

In addition to linear pathways that enable AND gates in human cells, natural TCS crosstalk provides additional types of logic control. For example, HK NarQ is capable of activating NarL almost as efficiently as NarX. Therefore a pathway in which humanized NarL is controlled by both NarX and NarQ was constructed and the response measured as the function of NarX and NarQ presence (FIG. 4A). Indeed, an almost perfect OR behavior is observed. The results indicate that complex logic is possible with naturally interacting pathways.

Known Mutant Behaviors are Recapitulated in the Mammalian Host

TCS research uncovered a large number of mutants that possess certain qualities that could be of use in synthetic pathways. For example, it is known that cytoplasmic domains of HKs result in constitutive signaling. A cytoplasmic domain of EnvZ (EnvZ cyt) was constructed and found that it supports constitutive signal transduction via OmpR. A mutant RR OmpR D55E is known to be a constitutive activator in bacteria, and its humanized version functions as a constitutive activator as well. Likewise, C-terminal domain of NarL (NarLc) is constitutive in bacteria and it remains a very strong inducer of NarL-RE in mammalian cells. This suggest that the findings made in the native prokaryotic setting translate into the humanized system, and that humanized pathways operate along the same mechanistic principles as they do in prokaryotes. They also illustrate that TCS-encoding genes and their variants can be used as a huge source of "biological parts" for mammalian gene circuits.

DISCUSSION

Histidine-aspartate phosphorelay is absent from vertebrate cells while it is found in plants, yeast, lower eukaryotes and most commonly in prokaryotes. The lack of homologous genes in vertebrates suggested prokaryotic TCS pathways as orthogonal signal processing modules in mammalian cells for circuit engineering. However, the preservation of the basic biochemical processes during mammalian "transplantation" was by no means guaranteed, as it required three conditions. First, the internal operation of a pathway has to be preserved as much as possible. Second, the pathway components should not affect the host nonspecifically. Third, the host should not interfere with the pathway components.

The inventors disclose herein that the phosphorelays between HK and RR, and differential DNA binding by the RR followed by gene induction, occur in mammalian cells. The presence of a cognate ligand does not seem to be necessary even though it modestly modulates pathway activity, at least in the case of DcuSR. However, the fact that full-length HK genes were functional suggests that they were properly folded and associated with a membrane. With respect to pathway effect on the host cells, no gross adverse effects were observed. The DNA binding sequences of the different RR are long and are not expected to occur frequently in the human genome. Finally, the response elements were silent in HEK293 cells on their own, meaning that no endogenous activator bound to these sites. RRs in combination with REs generated only low background expression, likely due to residual DNA binding of the non-phosphorylated RRs rather than due to phosphoryl transfer to the RR by endogenous kinases.

Among themselves, the pathways exhibited impressive lack of cross-reactivity. One unexpected interaction was uncovered between DcuS and OmpR. This cross-talk assay presents an attractive approach to study TCS biochemistry in vivo on the clean background devoid of interference. Even in the absence of response to external ligands, TCS can support complex logic signal integration in mammalian cells. Examples of AND, NOR and OR gates using constitutive and inducible HKs and RRs are disclosed in this invention. Given the difficulty to implement AND-like gene activation in mammalian cells, adapted TCS pathways are an attractive new source of such control elements. In addition, constitutive mutants act consistently with their behavior in prokaryotes; these mutants can be a rich source of simple and mutually-orthogonal building blocks in large gene circuits.

NarX-NarL, DcuS-DcuR, PhoR-PhoB, SenX3-RegX3, PhoQ-PhoP, RstB-RstA, CpxA-CpxR, CssS-CssR, CreC-CreB, BaeS-BaeR, BasS-BasR,QseC-QseB, KdpD-KdpE, TorS-TorR, ArcB-ArcA, TctE-TctD, ResE-ResD, VicK-VicR, MprB-MprA, MtrB-MtrA, PrrB-PrrA, TrcS-TrcR, NrsS-NrsR, ManS-ManR, NblS-NblR, SasA-RpaAB, SaeS-SaeR, BceS-BceR, YxdK-YxdJ, NarQ-NarP, UhpB-UhpA,

---

---

The invention claimed is:

1. An isolated mammalian cell comprising at least one prokaryotic two-component signaling (TCS) pathway comprised of
   i. an activator protein A,
   ii. a response regulator (RR) protein B activated by said protein A, such activation leading to an activated RR protein B, and
   iii. an output gene C operably linked to a promoter,
wherein transcription of the transcription apparatus in said isolated mammalian cell from said promoter is activated by activated RR protein B, and expression of output gene C defines at least a first state 0, which designates no transcription, and a second state 1, which designates detectable transcription, and
wherein said activator protein A is a sensor histidine kinase comprising a histidine residue, said RR protein B is a transcriptional regulator comprising an aspartic acid residue, and activation of said RR protein B by said activator protein A is effected by transfer of a phosphate from said histidine residue to said aspartic acid residue.

2. The isolated mammalian cell according to claim 1, wherein pairs of the activator protein A and said RR protein B are selected from the group consisting of EnvZ-OmpR, RcsC-RcsD-RcsB, BarA-UvrY, ComP-ComA, EvgS-EvgA, DegS-DegU, DesK-DesR, VraS-VraR, LiaS-LiaR, DevS-DevR, NreB-NreC, YdfH-YdfI, KinABCDE-Spo0FA, CitA-CitB, CitS-CitT, DctS-DctR, MalK-MalR, LytS-LytR, AlgZ-AlgR, NatK-NatR, AgrC-ArgA, ComD-ComE, GlnL-GlnG, NtrY-NtrX, HydH-HydG, AtoS-AtoC, PilS-PilR, GlrK-GlrR, PgtB-PgtA, DctB-DctD, KinB-AlgB, CheA-CheYBV, ChpA-ChB/PilGH, PixL-PixGH, WspE-WspRF, Cphl-Rcpl, PleC-PleD, CckA-CtrA/CpdR, LuxQN/CqsS-LuxU-LuxO, TtrS-TtrR, FlrB-FlrC, SLN1-YPD1-SSK1/SKN7, RpfC-RpfG, GlnK-GlnL, YesM-YesN, ChvG-ChvI, CiaH-CiaR, SalK-SalR, RegB-RegA and FixL-FixJ.

3. The isolated mammalian cell according to claim 1, wherein said protein A and said RR protein B are codon-optimized for human cells.

4. The isolated mammalian cell according to claim 1, wherein the output gene C encodes a fluorescent reporter, a protein or microRNA that affects the cell function or internal state.

5. The isolated mammalian cell according to claim 1, wherein the output gene C is amcyan.

6. The isolated mammalian cell according to claim 1, wherein the activator protein A can be constitutively active or activated by input signals.

7. The isolated mammalian cell according to claim 1, wherein the input signals are selected from the group consisting of: quinones, nitrate, nitrite, citrate, isocitrate, fumarate, succinate, malate, indole, serine, aspartate, chemoattractants, oxygen, carbon monoxide, nitrous oxide, blue light, vancomycin, potassium, quorum sensing molecules, temperature change, sulfate ions, nicotinic acid, changes in osmolarity, toluene, O-xylene, glutamine, 2-ketoglutarate, and magnesium.

8. An engineered biological logic AND gate comprising the isolated mammalian cell according to claim 1, wherein input 1 activates said activator protein A, input 2 activates said response regulator protein B and the output is the expression state of said output gene C.

9. The engineered biological logic AND gate according to claim 8, wherein input 2 activates a second activator protein A', which is able to activate a second RR protein B' that enables transcription of the first response regulator protein B.

10. The engineered biological logic AND gate according to claim 8, wherein input 1 and input 2 are stimuli selected from the group consisting of: quinones, nitrate, nitrite, citrate, isocitrate, fumarate, succinate, malate, indole, serine, aspartate, chemoattractants, oxygen, carbon monoxide, nitrous oxide, blue light, vancomycin, potassium, quorum sensing molecules, temperature change, sulfate ions, nicotinic acid, changes in osmolarity, toluene, O-xylene, glutamine, 2-ketoglutarate, magnesium and stimuli controlling expression of the components selected from transcription factors or microRNAs.

11. An engineered biological logic OR gate comprising the isolated mammalian cell according to claim 1, wherein input 1 activates said activator protein A, input 2 activates a second activator protein A' able to activate the same RR protein B as activator protein A and the output is the expression state of said output gene C.

12. An engineered biological logic NOR gate comprising the isolated mammalian cell according to claim 1, wherein input 1 is an inhibitor A− of said activator protein A, input 2 is an inhibitor B− of said RR protein B and the output is the expression state of said output gene C.

13. An engineered biological logic NAND gate comprising the isolated mammalian cell according to claim 1, wherein input 1 is an inhibitor A− of said activator protein A, input 2 is an inhibitor A'− of said activator protein A' and the output is the expression state of said output gene C.

14. The isolated mammalian cell according to claim 1, wherein pairs of the activator protein A and said RR protein B are selected from the group consisting of EnvZ-OmpR, NarX-NarL, and DcuS-DcuR.

\* \* \* \* \*